United States Patent [19]

Nagasaki et al.

[11] Patent Number: 4,653,478

[45] Date of Patent: Mar. 31, 1987

[54] ENDOSCOPE EQUIPMENT

[75] Inventors: Tatsuo Nagasaki, Musashino; Hiroyoshi Fujimori, Hachioji, both of Japan

[73] Assignee: Olympus Optical Co., Ltd., Tokyo, Japan

[21] Appl. No.: 656,375

[22] Filed: Oct. 1, 1984

[30] Foreign Application Priority Data

Sep. 30, 1983 [JP] Japan .................................. 58-183281
Oct. 3, 1983 [JP] Japan .................................. 58-184683
Oct. 3, 1983 [JP] Japan .................................. 58-184695

[51] Int. Cl.⁴ .............................................. A61B 1/06
[52] U.S. Cl. .................................................. 128/6
[58] Field of Search ............... 362/803, 293, 381, 321, 362/174; 355/38, 35; 353/84; 128/4–6; 356/274, 273, 276

[56] References Cited

U.S. PATENT DOCUMENTS

| Re. 31,290 | 6/1983 | Moore et al. | 128/6 |
|---|---|---|---|
| 1,141,124 | 6/1915 | Kobs et al. | 362/321 |
| 1,553,581 | 9/1925 | Weiler | 362/321 |
| 2,026,376 | 12/1935 | Colgate | 355/35 |
| 2,266,201 | 12/1941 | Heidel | 362/351 |
| 2,349,042 | 5/1944 | Holms | 362/321 |
| 2,362,431 | 8/1943 | Braunschmidt et al. | 355/35 |
| 2,578,562 | 12/1951 | Lapadura | 362/293 |
| 2,744,200 | 5/1956 | Taylor | 350/273 |
| 3,380,338 | 4/1968 | Mitchell | 355/35 |
| 3,832,054 | 8/1974 | Sable | 355/35 |
| 3,836,247 | 9/1974 | Weinert | 355/38 |
| 3,923,393 | 12/1975 | Inoue et al. | 335/55 |
| 4,074,306 | 2/1978 | Kakinuma et al. | 128/6 |
| 4,101,216 | 7/1978 | Grossmann | 355/38 |
| 4,475,539 | 10/1984 | Konomura | 128/6 |
| 4,480,636 | 11/1984 | Karaki et al. | 128/6 |
| 4,499,362 | 2/1985 | Martin | 350/274 |

FOREIGN PATENT DOCUMENTS

| 506973 | 6/1920 | France | 362/293 |
|---|---|---|---|
| 1122249 | 1/1955 | France | 350/273 |

Primary Examiner—Kyle L. Howell
Assistant Examiner—David Shay
Attorney, Agent, or Firm—Armstrong, Nikaido, Marmelstein & Kubovcik

[57] ABSTRACT

This invention concerns an endoscope using a line transfer type solid pickup element which is provided with a means to control the light incident upon the light receiving plane of the solid pickup element and accumulates the optical image from the subject during the incident period and reads the accumulated signal charges during the non-incident period. The means to control the incident light consists of the method to switch ON and OFF the light source driving voltage, method to switch ON and OFF the applied voltage of the liquid crystal filter provided in the optical path, method to provide a rotary filter with shielding regions in front of the light source and method to use a strobo light source. Furthermore, in order to display in color, the combination with the R, G and B color filters is used.

3 Claims, 21 Drawing Figures (b)

ENDOSCOPE EQUIPMENT

BACKGROUND OF THE INVENTION

This invention concerns an endoscope using a line transfer type solid state image sensing element suitable for miniaturization.

Recently, various kinds of endoscopes using solid state image sensing elements, such as charge coupled devices for the image sensing means, are being proposed.

The endoscopes using the aforementioned solid stage image sensing elements have the advantages that it is possible to prevent the quality of pictures from deteriorating due to the breaking of fibers in the endoscope using the image guide made of an optical fiber bundle and that it is easy to record pictures, and it is expected that they will be increasingly used in the future because further miniaturization and improvement of resolving power can be expected, as the integration technology makes progress.

As the solid state image sensing element, the charge coupled device (CCD) having two functions of photoelectric conversion and scanning is widely used. This CCD is roughly divided into a frame transfer type, a line transfer type and a vertical inter-line type.

In the frame transfer type CCD, firstly photoelectric conversion and signal accumulation are made at a light sensing part during a field period and the charges are put in parallel and transferred to and accumulated in an accumulating part during the short time of a vertical blanking period, and the shielded charges in the accumulating part equivalent to 1 scanning line are transferred in the standard scanning method by means of the horizontal register during the horizontal blanking period, and the signals are sequentially read out.

The line transfer type CCD is provided with a vertical output register and reads out the signals by switching the transferred signals per line.

In the vertical inter-line transfer type CCD, the light sensing part and transferring part are paired and arranged in a line in the longitudinal direction.

The line transfer type CCD can be made smaller than other types of CCD, but it has a disadvantage that when charges are transferred for signal reading, the incident light is received and the signal charge corresponding to a different picture element is superimposed and the smear phenomenon (picture becomes indistinct) occurs.

BRIEF SUMMARY OF THE INVENTION

The objective of this invention is to provide an endoscope using the line transfer type solid state image sensing element which can prevent the smear phenomenon and give clear pictures.

Another objective of this invention is to provide an endoscope whose end part can be made small in diameter.

Still another objective of this invention is to provide an endoscope which can be used even in a narrow body cavity part through miniaturization, thus expanding the scope of application of the endoscope.

Other features and benefits of this invention will be made clear by the following explanation.

DETAILED DESCRIPTION OF THE EMBODIMENTS

Figure 1:
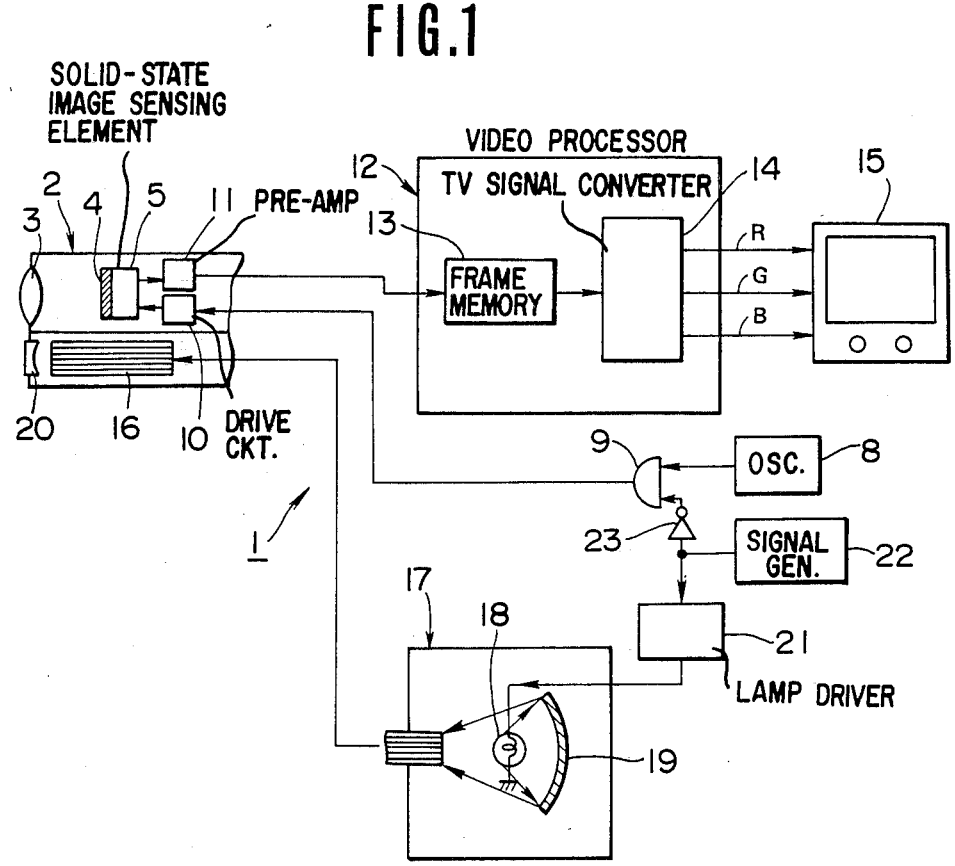
FIG. 1 is a block diagram to show Embodiment 1 of the endoscope related to this invention.
Figure 2:
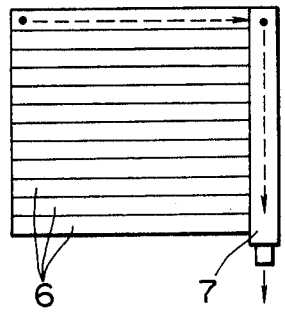
FIG. 2 is a front view to show an approximate makeup of the line transfer type solid state image sensing element.
Figure 3:
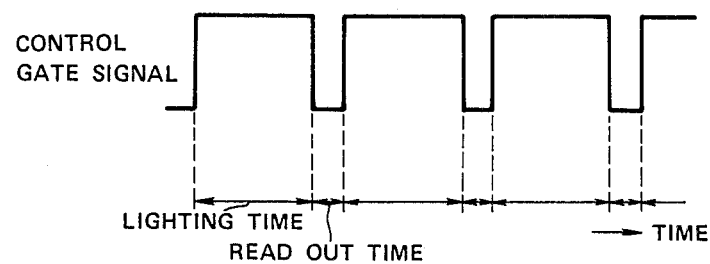
FIG. 3 is an explanatory diagram to show the relationship among the control gate signal, lighting time and readout time in the device in FIG. 1.

FIGS. 1 to 3 concern the first Embodiment of this invention.

As shown in FIG. 1, a hard end component 2 is provided continuously at the front end side of a narrow and flexible inserting member of the endoscope 1 which can be inserted into a body cavity, etc.

The observation window of the said end part 2 is provided with an object lens 3 for image-forming, and at the focal point of the said object lens 3 a line transfer type solid state image sensing element 5 with the tri-color mosaic filter 4 at the front thereof is provided.

On the image sensing plane of the solid state image sensing element 5, as shown in FIG. 2, the line light sensing part 6 consisting of many light receiving elements arranged in the horizontal direction is formed and the signal charges can be transferred and read from the output register 7 by applying the readout clock signals of the specified phase relationship. The signal change is output by switching the transfer signal for each line.

The transfer signal to be switched for each line and the readout clock signal of the specified phase relationship are formed by the drive circuit 10 which takes in the reference clock signal output from the oscillator 8 via the AND circuit 9. When the output signal from the drive circuit 10 is applied, the signal read from the solid state image sensing element 5 is amplified in low noise factor by the preamplifier 11, passed through the signal line, and written in the frame memory 13 in the video processor 12.

The signal written in the frame memory 13 is separated and converted into 3 color signals R, G and B on which the horizontal and vertical signals are superposed in the TV signal converter 14 and displayed on the color TV monitor 15. For writing into the frame memory 13, the signals are AD-converted into digital values and after being read out, they are DA-converted into analog values.

In the inserting member a light guide 16 made of a flexible optical fiber bundle is inserted for transmitting the illuminating light from a light source to the object. The rear end of the said light guide 16 is attached in a removable way to the light source equipment 17. The illuminating light of the lamp 18 in the light source equipment 17 is reflected by the concave plane of the reflector 19 and condensed and then projected to the rear end face of the light guide 16, and the light is transmitted through the light guide 16 and projected from the front end face fixed in the end part 2 through the light distributing lens 20 to the subject in order for an image can be formed on the image sensing plane by the object lens 3.

The illuminating lamp 18 is driven with the power supplied from the lamp driver 21 and the power supplied to and cut off from the lamp driver 21 is controlled by the control gate signals (shown in FIG. 3) output from the control gate signal generator 22, i.e. when the control gate signal is on a high level, the power is supplied to the illuminating lamp 18 and when low level, the supply is stopped. The above control gate signal is, for example, for high level at 29 msec. and low for 4 msec. (not limited to this).

The above control gate signal is applied to the other input end of the AND gate circuit 9 via the inverter circuit 23 and only when the level of the signal applied to the input end is high (i.e. control gate signal is at low level), the reference clock signal from the oscillator 8 is output to the drive circuit 10 (i.e. the readout time shown in FIG. 3). That is, the control gate signal generator 22 causes the illuminating lamp 18 to light and to illuminate the subject during the lighting time when the control gate signal is at high level, and the subject image is formed on the image sensing plane by means of the reflected light from the subject, resolved into the picture element units and received by the light receiving elements and accumulated as charges, and control is made so that the reference clock signal for signal reading is not output to the drive circuit 10, and during the readout time when the control gate signal is at low level, the AND circuit 9 is opened, the reference clock signal is supplied to the drive circuit 10, and the illuminating lamp 18 is extinguished to prevent the light from entering the light receiving elements.

In the first Embodiment thus formed, by means of the control gate signal, the subject is lighted during the lighting time and the reflected light from the subject is received by the light receiving elements and accumulated as charges. During the subsequent readout time when the accumulated charges are sequentially read out by means of the output signal of the drive circuit 10, the illuminating lamp 18 is extinguished to prevent the incident light from being received by the light receiving elements, and therefore, the signals can be read without occurrence of the smear phenomenon.

The read signals are amplified by the preamplifier 11 and written into the frame memory 13 in the video processor 12. During the subsequent lighting time, they are read out sequentially, separated into R, G and B color signals by the sample hold circuit in the TV signal converter 14, superposed on by horizontal and vertical synchronizing signals, applied to the RGB terminals in the color TV monitor 15 to display the subject in color.

The above first Embodiment can make it possible to make small the outside diameter of the end part 2 to contain the solid state image sensing element 5 because it uses a line transfer type solid state image sensing element 5 with small area which is not provided with the transfer part to accumulate the charges received by the light receiving elements forming the light sensing part 6 as well as preventing the smear phenomenon.

Figure 4:
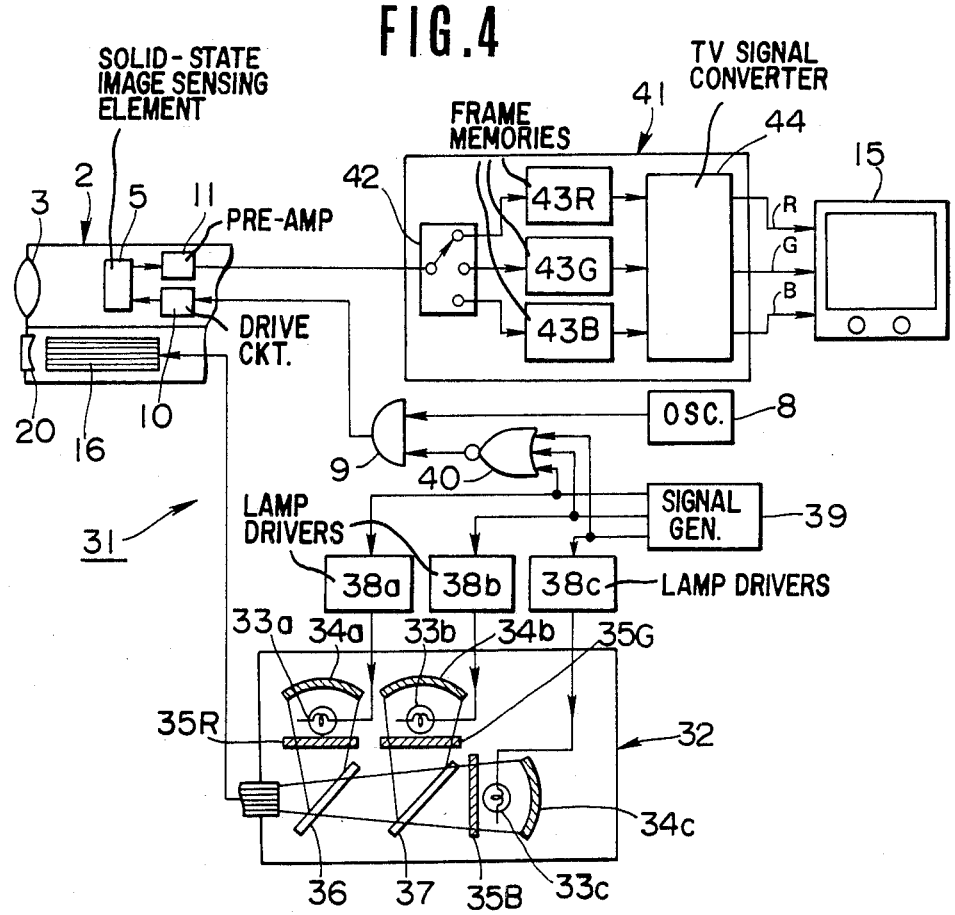
FIG. 4 is a block diagram to show a second Embodiment of the endoscope of this invention.

FIG. 4 shows a second Embodiment of this invention.

This embodiment uses a line transfer type solid state image sensing element 5 (for black and white) which is not provided with tri-color mosaic filter 4 used in the first Embodiment and the lighting means illuminates sequentially in the light of each wavelength of 3 colors.

That is, in this endoscope 31, 3 illuminating lamps 33a, 33b and 33c are provided in the light source equipment 32. The illuminating light of the illuminating lamp 33a is reflected and condensed by the reflector 34a and only the red light is transmitted through the red transmission filter 35R and the red light is further reflected by the half mirror 36 and irradiated to the rear end face of the light guide 16.

The illuminating light of the illuminating lamp 33b is reflected and condensed by the reflector 34b, transmitted through the green transmission filter 35G to become the light with green wavelength, reflected by the half mirror 37, and irradiated to the rear end face of the light guide 16.

Furthermore, the illuminating light of the illuminating lamp 33c is reflected and condensed by the reflector 34c, transmitted through the blue transmission filter 35B to become the light with blue wavelength, and irradiated to the rear end face of the light guide 16 via the above half mirrors 37 and 36.

The above illuminating lamps 33a, 33b and 33c are supplied with the lamp driving output from the red, green and blue lamp drivers 38a, 38b and 38c respectively. The output (power) supplied to and cut off from the lamp drivers 38a, 38b and 38c are controlled by the control gate signals output from the output terminals of the control gate signal generator 39 as in the case of the first Embodiment.

The above control gate signals are applied to the other input terminal of the AND circuit 9 via the NOR circuit 40 with 3 inputs and when any of the 3 control gate signals is at high level, the gate of the AND circuit 9 is closed, and when the 3 control gate signals are at low level, the gate is opened to supply the reference clock signal of the oscillator 8 to the drive circuit 10 and the signals are read and during this period, the illuminating lamps 33a, 33b and 33c are extinguished so that the reflected light from the subject is not received by the light receiving elements.

Figure 5:
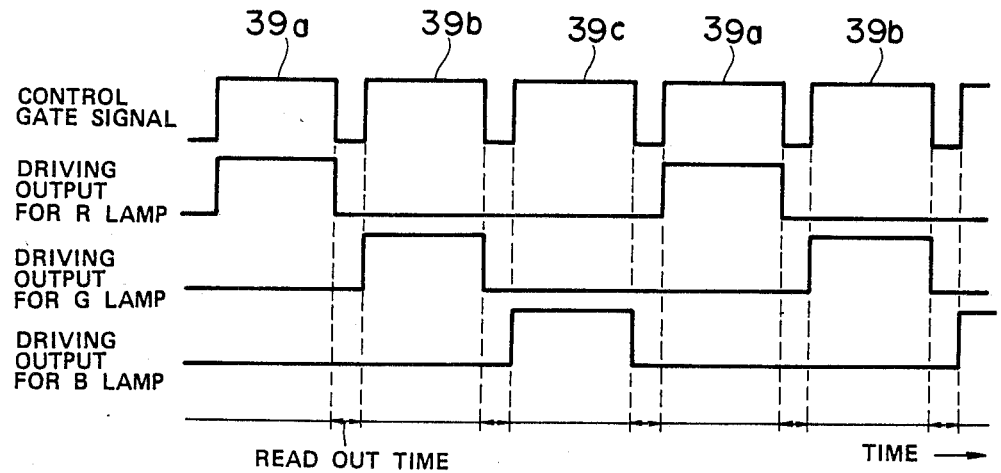
FIG. 5 is a timing chart to show the dynamic relations between the control gate signals and line driving output in the device of FIG. 4.

The above control gate signal generator 39 sequentially outputs from its output terminals the control gate signals 39a, 39b and 39c which become high level for a certain period (illuminating period) and are then kept low for a specified period (readout period) as shown in FIG. 5. During each control gate period when these control gate signals 39a, 39b and 39c sequentially become high level, each of the driving output for R lamp, G lamp and B lamp (Refer to FIG. 5) is output to sequentially light the illuminating lamps 33a, 33b and 33c and the illuminating lights are sequentially transmitted through the red, green and blue transmission filters 35R, 35G and 35B to sequentially illuminate the subject in the light of each wavelength of red, green and blue.

For the image of a subject illuminated by each light of the 3 primary colors and formed on the image sensing plane by means of the reflected light from the subject, the signals of 1 frame of each color of light is read out during each readout time, amplified by the preamplifier 11, and then written into the frame memories 43R, 43G and 43B conducted by the said multiplexer 42 via the multiplexer 42 in the video processor 41. After the signals of 1 frame for each color are written, the signals written in the frame memories 43R, 43G and 43B are read out simultaneously for 3 colors, superimposed with horizontal and vertical synchronizing signals in the TV signal converter 44 to become R, G and B color signals and displayed on the color TV monitor 15.

The above multiplexer 42 can be sequentially switched synchronized with the readout time when the control gate signals 39a, 39b and 39c are at low level.

In the second Embodiment 1 thus formed, a subject is illuminated sequentially by the light of each wavelength of the 3 primary colors and the image is received and accumulated by the light receiving elements, and when the signals are read out, the illuminating light is extinguished, thus making it possible to prevent the smear phenomenon.

Therefore, it can use a line transfer type solid state image sensing element 5 with small area as in the case of the first Embodiment. Thus the end part 2 can be made small in diameter, and can alleviate the pain of the patient when it is inserted into the body cavity.

In the endoscope 31 of the second Embodiment which uses 3-color sequential lighting means, the image can be sensed by using all the light receiving elements for each color under each color lighting, and therefore, a higher resolving power can be obtained than in the first Embodiment.

In the above embodiments, the lamps 18, 33a, 33b and 33c in the light source devices 17 and 32 are used as light source, but this invention is not limited to these lamps, and for example, an illuminous diode can also be used. In case the illuminous diode is used, it can also be provided on the side of end part 2 of the endoscopes 1 and 31, and thus the light guide 16 is not always required. Also, a miniature lamp, etc. can be contained in the end part 2. The above light source is controlled by means of the control gate signal so that it is extinguished during the signal readout period.

In case the illuminous diodes are used, if the illuminous diodes emit light of the 3 primary colors and are sequentially lighted, the filters 35R, 35G and 35B in the second Embodiment are not always necessary.

In the above embodiments, it is explained that the R, G and B color signals are output from the video processors 12 and 41, but they may also be output as the NTSC type or other color TV signals. It is also possible to display sequentially the R, G and B color signals in the unit of frame and observe them as color pictures utilizing the residual image.

The tri-color filter in the first Embodiment is not limited to the color mosaic filter 4, and for example, 3 primary color filters arranged in stripes may be also used.

In the above embodiments, the illuminating lamps 18, 33a, 33b and 33c are extinguished during the signal readout period so that the light will not be received by the light receiving elements during this period. However this invention is not limited to this, and for example, a liquid crystal filter can be provided between the rear end face of the light guide 16 and the light source such as the illuminating lamps 18, 33a, 33b and 33c, thus controlling the application of voltage to the liquid crystal filter.

The above liquid crystal filter is not limited to the installation in the light source equipment 19 or 32, and the same function can be obtained by providing it between the light distributing lens 20 and the front end face of the light guide 16 (or a light source such as illuminous diode), for example, at the pupil position of the distributing lens 20.

Furthermore, the above liquid crystal filter can be provided in front of the image sensing plane or at the pupil position of the object lens 3 and control can be made so that the light is not received by the light receiving elements during the signal readout time (although illuminated). The important thing is that the light is not received by the light receiving elements of the light sensor 6 of the line transfer type solid state image sensing element during the signal readout time.

Figure 6:
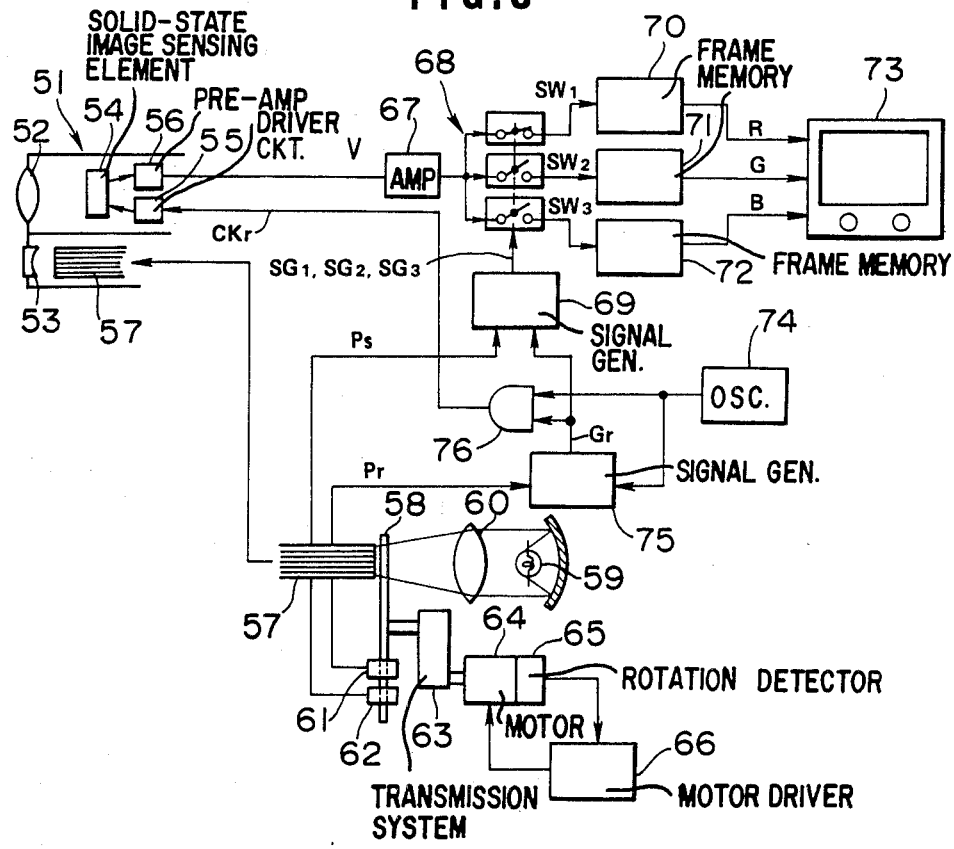
FIG. 6 is a block diagram to show a third Embodiment of this invention.
Figure 7:
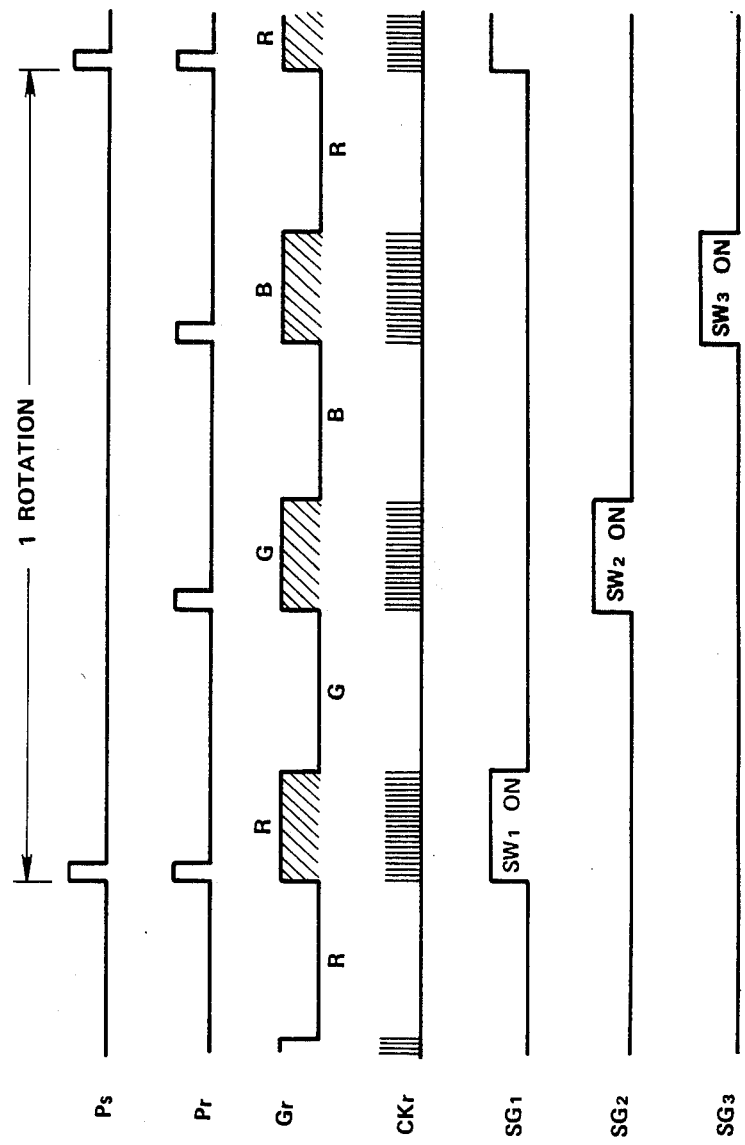
FIG. 7 is a timing chart to explain the operation of the equipment in FIG. 6.

FIG. 6 shows a block diagram of a third Embodiment of this invention, and FIG. 7 is a timing chart to explain the operation.

In FIG. 6, the sign 51 indicates the end component of the inserting member of an endoscope, and at the end an object lens 52 and illuminating lens 53 are provided in parallel. Behind the object lens 52 a line transfer type solid state image sensing element 54 is provided, and the optical image received is converted into video signals by the driver circuit 55 and the video signals V are sent to the next-stage circuit via the preamplifier 56. Behind the illuminating lens 53, a light guide 57 made of an optical fiber bundle, etc. is provided, and the illuminating light is projected onto the rear end face of the optical fiber bundle through the rotary filter 58. The illuminating light from the light source lamp 59 is projected onto the rotary filter 58 through the lens 60 and then onto the end face of the light guide 57 via the R, G and B filters alternately provided at a suitable shielding period in the filter 58. For the outer periphery of the rotary filter 58, the readout pulse detector 61 and start pulse detector 62 are fixed, and the rotary filter 58 rotates on the rotating shaft at a specified speed. The rotating shaft is connected to the motor 64 via the transmission system 63, and the signal from the rotation detector 65 provided in the motor 64 controls the motor driver 66 to make the rotating speed of the motor 64 constant. On the other hand the video signal V from the above preamplifier 56 is amplified by the amplifier 67 and input to the multiplexer 68. The multiplexer 68 consists of 3 switches SW1, SW2 and SW3 corresponding to the R, G and B signals input. These switches are sequentially switched in a specified frame cycle by means of the switching gate signals $SG_1$, $SG_2$ and $SG_3$ from the gate signal generator 69 for multiplexer, and the signals are accumulated in the R, G and B frame memories 70, 71 and 72 and then displayed on the color TV monitor 73 through the R, G and B signal lines. The readout pulse detector 61 is to detect the final end position of the R, G and B filters provided in the rotary filter 58 in the rotating direction and the detected pulse (readout pulse) Pr and the signals from the oscillator 74 are used by the readout gate signal generator 75 to produce the readout gate signal Gr. The readout gate signal Gr is to read out the video signals accumulated in the solid state image sensing element 54 during the period corresponding to the period when the R, G and B lights are not irradiated and it, together with the signal from the oscillator 74, is input to the AND circuit 76 to produce the readout clock signal CKr and drive the driver circuit 55 to convert the accumulated charges in the solid state image sensing element 54 into the video signal V for each of R, G and B. Also the readout gate signal Gr, together with the detected pulse (start pulse) Ps from the start pulse detector 62 (which detects one rotation of the rotary filter 58), is input to the gate signal generator 69 for multiplexer to produce the switching gate signals $SG_1$, $SG_2$ and $SG_3$, to switch the multiplexer 68 and to input the R, G and B video signals to the frame memories 70, 71 and 72.

In such makeup, as shown in FIG. 7, every time the rotary filter 58 makes one rotation, one start pulse Ps is output and sent to the gate signal generator 69 for multiplexer and 3 readout pulses Pr corresponding to the R, G and B filters are sent to the readout gate signal generator 75. The readout gate signal generator 75 produces the readout gate signal Gr of the width corresponding to the period when the R, G and B lights are not irradiated, in the same cycle as the readout pulse Pr, using the signal from the oscillator 74. On the basis of the period of the readout gate signal Gr, the readout clock signal CKr and switching gate signal $SG_1$, $SG_2$ and $SG_3$ are produced and the R, G and B signals necessary for color display are obtained. In the illustration of the readout gate signal Gr, the oblique line parts are the R, G and B video signal readout periods and the low level periods are the periods when the R, G and B lights are irradiated and the R, G and B signal charges are accumulated in the solid state image sensing element 4. Therefore, the switching gate signals $SG_1$, $SG_2$ and $SG_3$ for the R, G and B frame memories 70, 71 and 72 become the gate signals corresponding to the R, G and B video signal readout periods.

Figure 8:
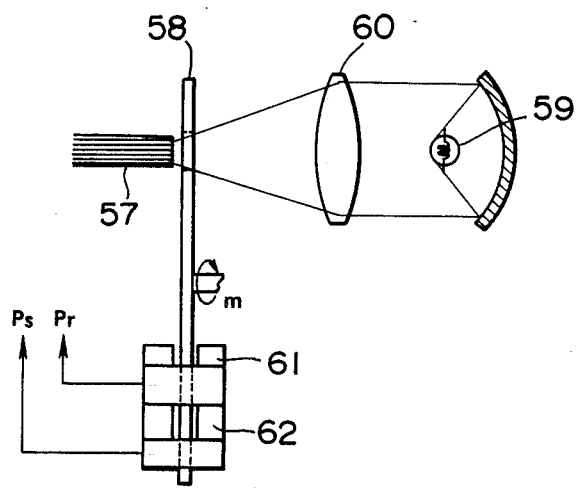
FIG. 8 is a side view to show an enlarged rotary filter portion of FIG. 6.
Figure 9:
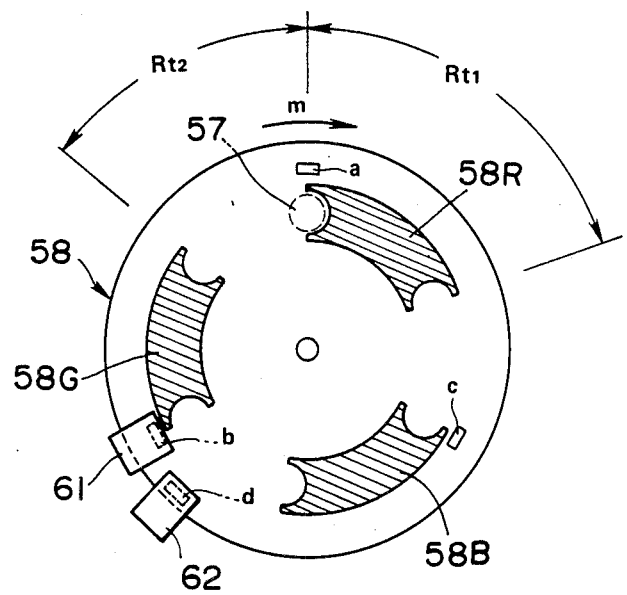
FIG. 9 is a front view to show an embodiment of the rotary filter used in the device of FIG. 6.

FIG. 8 is an enlarged side view to show the above rotary filter 58 and FIG. 9 shows an embodiment of the rotary filter 58.

As shown in these figures, the rotary filter 58 has, for example, 3 transmission windows arranged at a specified interval on a light shielding disk and these transmission windows are provided with R, G and B filters 58R, 58G and 58B. The transmission windows are elongated in the rotating direction m and both ends are concave. In the periphery of the shielding disk at the positions (final end position when each filter rotates) corresponding to the R, G and B filters 58R, 58G and 58B, 3 holes a, b and c are formed on the same circumference. In order to detect these holes a, b and c when rotating, a photo interrupter 61 for detecting the readout pulse is fixed with respect to the rotary filter 58 at the outer periphery. At a further periphery than the holes a, b and c, one hole d is formed and in order to detect one rotation of the rotary filter 58 by detecting the hole d, a photo-interrupter 62 for detecting the start pulse is also fixed with respect to rotary filter 58 at the outer periphery thereof. The photo-interrupters 61 and 62 can be made of Hall element or magnetic thin film element utilizing magnetism as well as photo-coupler.

In the above makeup, as shown in FIG. 9, when the rotary filter 58 rotates in the arrow m direction, the R, G and B filters 58R, 58G and 58B and the shielding faces along them are sequentially moved toward the end face of the light guide 57, and therefore, after a certain shielding period, the illuminating light from the light source lamp 59 is put in the light guide 57 via the R, G and B filters and projected onto a subject through the illuminating lens 53. The reflected light from the subject is received by the solid state image sensing element 54 through the object lens 52 and is converted into video signals n such a case, for example, during a period $Rt_1$ when the end face of the light guide 57 is covered by the R filter 58R, R light is projected onto the subject and the reflected light is received by the solid state image sensing element 54 and accumulated as video signals. Subsequently when the shielding period $Rt_2$ starts, the light is not projected during this period $Rt_2$ and the video signals already accumulated in the solid state image sensing element 54 by means of the R light are read out.

Figure 10:
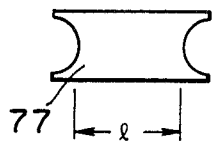
FIGS. 10 to 12 are front views to show the shape of R, G and B filter of the rotary filter.
Figure 11:
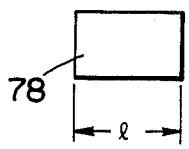
Figure 12:
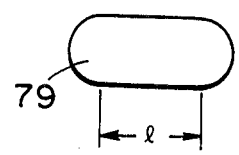
Figure 13:
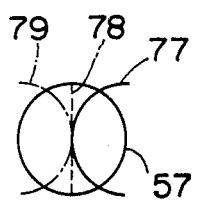
FIG. 13 is an explanatory diagram to show the operation by means of the filter shapes shown in FIGS. 10 to 12.
Figure 13:
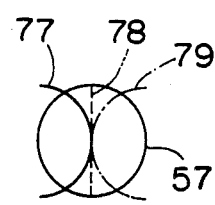
Figure 14:
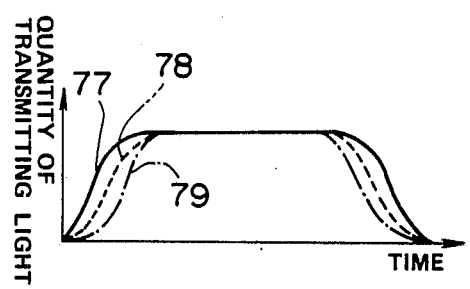
FIG. 14 is an explanatory diagram to show the rising and falling characteristics of the quantity of transmitting light by means of the filter shapes shown in FIGS. 10 to 12.

In such a case, the ends of the transmission windows formed in the shielding disk of the rotary filter 58 (i.e. the shape of R, G and B color filters) can be made concave (77) as shown in FIG. 10, straight (78) as shown in FIG. 11 or convex (79) as shown in FIG. 12. If the color filters of different shapes like the ones shown in FIGS. 10, 11 and 12 are formed in the rotary filter 58, the starting end position of the color filters 77, 78 and 79 covers the end face of the light guide 57 (i.e. incident luminous flux) as shown in (a) of FIG. 13 when the filter 58 rotates, thus starting the incident stage and in such a case, of the 3 filter shapes 77, 78 and 79, the filter shape 77 shown in FIG. 10 has the fastest rise time of light quantity. When the filter 58 further rotates, the final end position of the color filters 77, 78 and 79 covers the end face of the light guide 57 as shown in (b) of FIG. 13 to start the light shielding stage, and in such a case, the filter shape 77 has the fastest fall time of the light quantity. If the color filter shapes 77, 78 and 79 shown in FIGS. 10 to 12 are actually compared on the quantity of transmitted light when the rotary filter 58 rotates, the result as shown in FIG. 14 is obtained and from this result it is known that both rise time and fall time of the light quantity can be minimized with the shape 77 shown in FIG. 10. But in FIGS. 10 to 12, the length l of the band portion in the rotating direction, i.e. the portion without the special shapes on the ends, is same. In order to maximize the period of the light quantity, as shown in FIG. 9 each one of the R, G and B filters 58R, 58G and 58B can be arranged in the rotary filter 58 and the longest distance l can be set within the range where necessary readout time $Rt_2$ can be secured.

Figure 15:
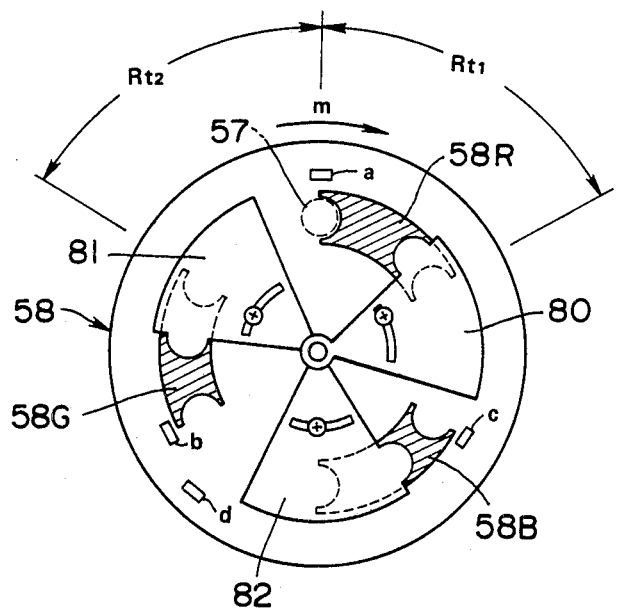
FIG. 15 is a front view to show another embodiment of the rotary filter used in the device of FIG. 6.

FIG. 15 is a front view to show another embodiment of the rotary filter 58. In the rotary filter 58 shown in this embodiment, the shape and arrangement of the transmission windows formed in the shielding plate and the arrangement of the R, G and B filters 58R, 58G and 58B provided in the transmission windows are completely same as those in the embodiment shown in FIG. 9 but the difference is that the variable shielding plates 80, 81 and 82 which are pivoted around the rotating shaft and can control the shielding range (i.e. transmission range) by means of adjusting screw are provided to adjust the opening area of the R, G and B filters 58R, 58G and 58B. The variable shielding plates 80, 81 and 82 are provided on the starting end side of the filters 58R, 58G and 58B when they rotate and each filter is independently adjusted. The shape of the filters 58R, 58G and 58B remains the same shape shown in FIG. 10 even when they are shielded by the variable shielding plates 80, 81 and 82.

Figure 16:
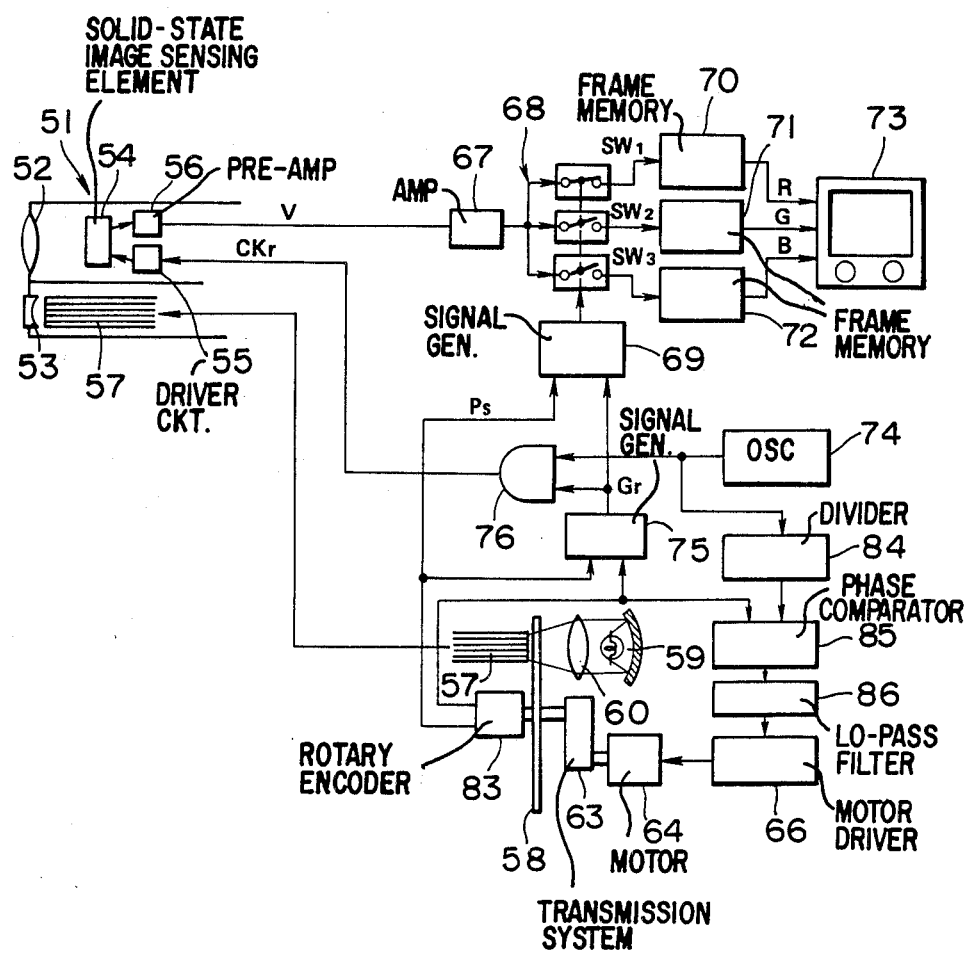
FIG. 16 is a block diagram to show a fourth Embodiment of this invention.

FIG. 16 shows a fourth Embodiment of this invention. The makeup of the rotary filter 58 is same as the one shown in FIG. 9 or FIG. 15, but instead of the readout pulse detector 61 and start pulse detector 62, a rotary encoder 83 is provided on the rotating shaft of the rotary filter 58 and the readout gate signal Gr is produced by the readout gate signal generator 75 using the signal detected by the rotary encoder 83 and the start pulse Ps. The detected signal of the rotary encoder 83 and the signal from the oscillator 74 divided by the divider 84 are input to the phase comparator 85 to detect the phase difference. Then, the detected signal is fed back to the motor driver 66 through the low pass filter circuit 86 to control the speed of the motor 64 to be constant. Other circuit makeup than the above remains same as that in FIG. 6.

In FIGS. 9 and 15, one each of the R, G and B color filters 58R, 58G and 58B is arranged in a suitable shielding region on the same circumference of the rotary filter 58, but it is also possible that more of each filter are arranged on the same circumference via the shielding region.

Figure 17:
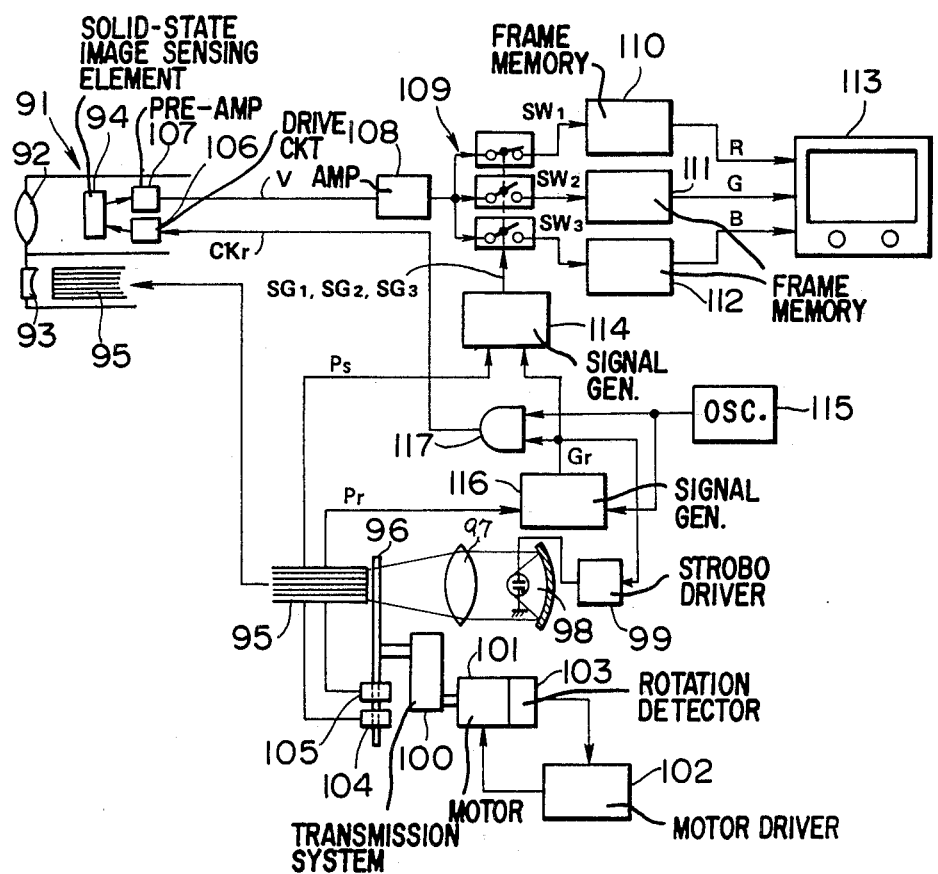
FIG. 17 is a block diagram to show a fifth Embodiment of this invention.
Figure 18:
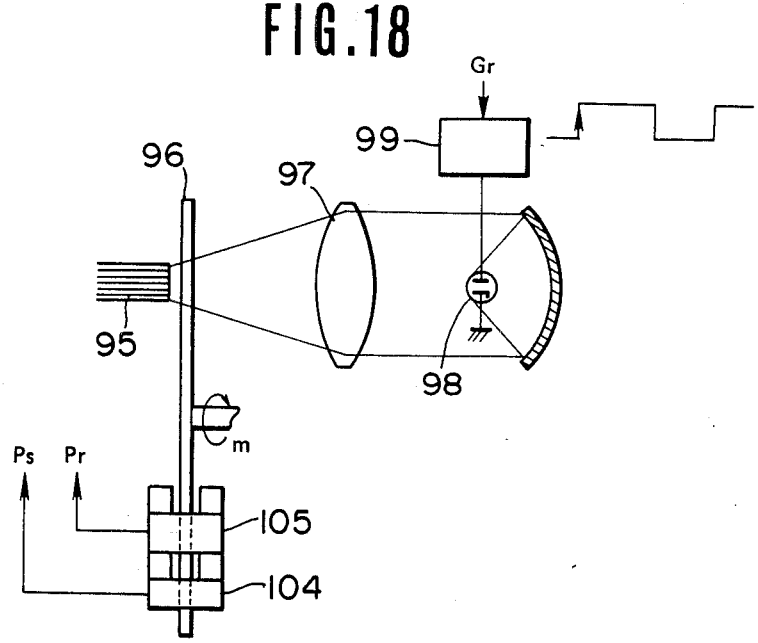
FIG. 18 is a side view to show an enlargement of the rotary filter portion and light source portion of FIG. 17.
Figure 19:
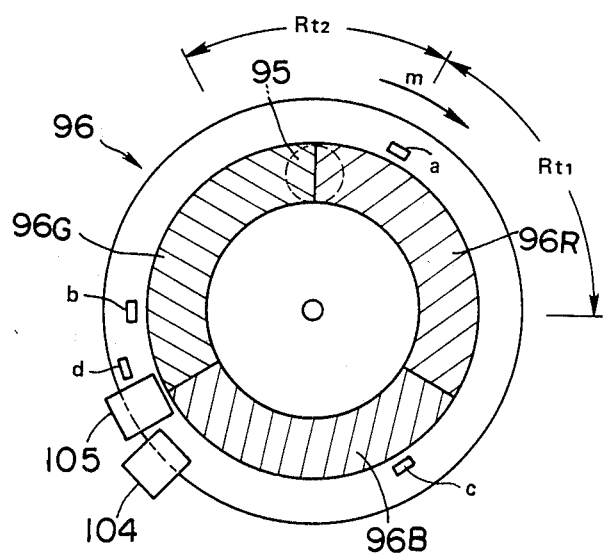
FIG. 19 is a front view to show the rotary filter used in the equipment of FIG. 17.

FIG. 17 is a block diagram to show a fifth Embodiment of this invention and FIGS. 18 and 19 are a side view and front view respectively to show the makeup of the rotary filter.

In FIG. 17, the reference numeral 91 indicates the end component of the inserting member of an endoscope and at the end thereof, the object lens 92 and illuminating lens 93 are provided in parallel. Behind the object lens 92 a line transfer type solid state image sensing element 94 is provided and the optical image of a subject is received and formed on its light receiving plane. On the other hand, behind the illuminating lens 93 a light guide 95 made of an optical fiber bundle, etc. is provided. At the rear end of the light guide 95 a rotary filter 96 is provided with the rotating plane facing the rear end of the light guide 95 and behind the rotary filter 96, a condenser lens 97 and strobo lamp 98 (e.g. xenon strobo lamp) are provided and through the rotary filter 96 the illuminating light is projected onto the light guide 95. The strobo lamp 98, as shown in FIG. 18, is driven with the driving signal from the strobo driver 99 which is operated by means of the readout gate signal Gr and is lighted and extinguished repeatedly in a given cycle. The rotary filter 96, as shown in FIG. 19, is provided on its rotating plane with the R, G and B color filters 96R, 96G and 96B which are elongated and alternate on the same circumference, and when rotating (in the arrow m direction), the illuminating light is transmitted sequentially through the R, G and B filters 96R, 96G and 96B and projected onto the light guide 95. The rotating shaft of the rotary filter 96 is connected to the motor 101 via the transmission system 100 and the motor is driven by means of the motor driver 102. The motor 101 is provided with a rotation detector 103 and the detected signal controls the motor driver 102 to keep the rotating speed constant. Furthermore, in the rotating plane of the rotary filter 96 holes a, b, c and d are formed and on the periphery of the rotary filter 96 the start pulse detector 104 and readout pulse detector 105 are provided. The start pulse detector 104 outputs the start pulse Ps every rotation by detecting the hole d formed on the same circumference and the readout pulse detector 105 outputs 3 readout pulses Pr every rotation by detecting the holes a, b and c formed at equal intervals on the same circumference. The start pulse detector 104 and readout pulse detector 105 can be made of Hall elements or magnetic thin film elements as well as the photo interrupter. Then, the R, G and B lights projected through the light guide 95 and illuminating lens 93 sequentially light the subject and the reflected light is sequentially received by the solid state image sensing element 94 and accumulated as signal charges. The charges accumulated in the solid state image sensing element 94 are converted into electrical signals separately for R, G and B by means of the driver circuit 106 driven by the readout clock signal CKr, and through the preamplifier 107, they are input as the R, G and B video signals V to the next stage amplifier 108. The amplified output of R, G and B is sequentially switched in the multiplexer 109, accumulated in the next R, G and B frame memories 110, 111 and 112, read out from these memories and output and displayed on the color TV monitor 113. The multiplexer 109 consists of 3 switches $SW_1$, $SW_2$ and $SW_3$ corresponding to the R, G and B signals and these switches are sequentially switched by means of the switching gate signals $SG_1$, $SG_2$ and $SG_3$ from the gate signal generator 114 for multiplexer. The reference numeral 115 refers to an oscillator to oscillate signals with specified frequency and the signal from this oscillator 115, together with the detection pulse Pr from the readout pulse detector 105, is input to the readout gate signal generator 116 to produce the readout gate signal Gr. The readout gate signal Gr, together with the signal from the oscillator 115, is input to the AND circuit 117 and the readout clock signal CKr is output to the driver circuit 106. The readout signal Gr, together with the detection pulse Ps from the start pulse detector 104, is input to the gate signal generator 114 to produce the 3 switching gate signals $SG_1$, $SG_2$ and $SG_3$ to switch the switches $SW_1$, $SW_2$ and $SW_3$ of the multiplexer 109.

Figure 20:
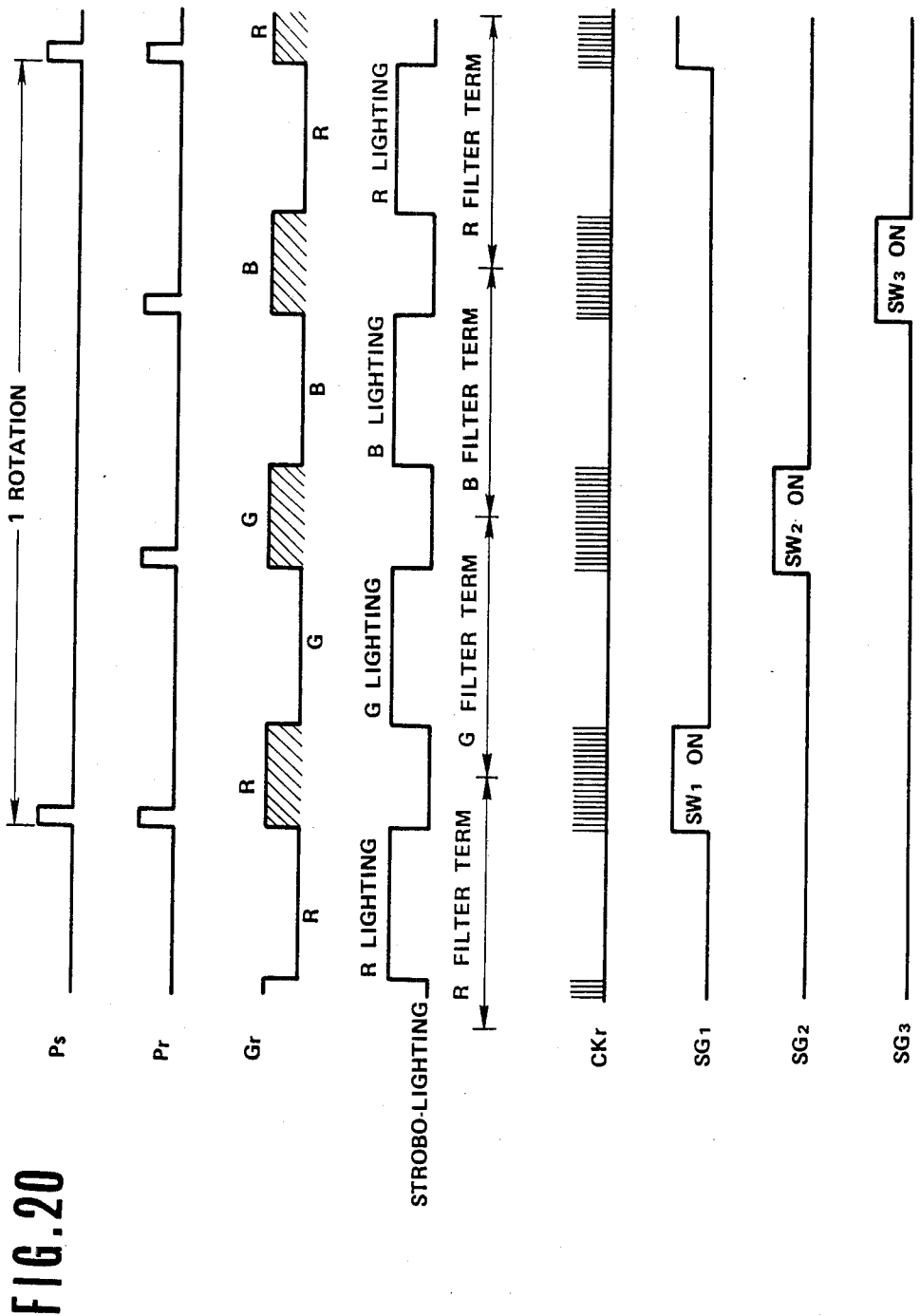
FIG. 20 is a timing chart to explain the operation of the device of FIG. 17.

The following will explain the operation referring to the timing chart shown in FIG. 20.

As shown in FIG. 20, every time the rotary filter 96 makes one rotation, 1 start pulse Ps is output and sent to the gate signal generator 114 for multiplexer and 3 readout pulses Pr corresponding to the R, G and B filters 96R, 96G and 96B are output and sent to the readout gate signal generator 116. The readout gate signal generator 116 produces the readout gate signal Gr in the same cycle as the readout pulse Pr using the signals from the oscillator 115. In accordance with the term of this readout gate signal Gr, the strobo driver 99 is operated to light or extinguish the strobo lamp 98. As shown in FIG. 19, the holes a, b and c on the rotary filter 96 are formed in the positions a certain distance shifted in the rotating m direction from the border positions of the R, G and B filters 96R, 96G and 96B. In the rotating process of the rotary filter 96, for example, in the case of the R filter 96R, the section $Rt_1$ from a specified position in the filter region to the hole a is equivalent to the lighting period by means of the R light, and during this period, the strobo lamp 98 is lighted and the R light is irradiated through the light guide 95 and the reflected light is received by the solid state image sensing element 94. And the section $Rt_2$ from the transmission hole a to a specified position of the G filter 96G is equivalent to the readout period and during this period the strobo lamp 98 is extinguished and the charges accumulated in the solid state image sensing element 94 by means of the R light are read out and output as the video signal V. Therefore, the ON and OFF operation of the strobo lamp 98 is corresponding to the period of the readout gate signal Gr as shown in FIG. 20. In the illustration of the readout gate signal Gr, the oblique line parts are the R, G and B video signal readout periods and the preceding low level periods are the period when the R, G and B signal charges are accumulated in the solid state image sensing element 94 by means of the R, G and B lights. On basis of the readout gate signal Gr periods the readout clock signal CKr and switching gate signal $SG_1$, $SG_2$ and $SG_3$ are produced and the R, G and B signals necessary for color display are obtained. Therefore, the switching gate signals $SG_1$, $SG_2$ and $SG_3$ to switch the R, G and B frame memories 110, 111 and 112 respectively become the gate signals to correspond to the R, G and B video signal readout periods. Since, as aforementioned, the signal accumulation in and signal reading from the line transfer type solid state image sensing element are performed synchronized with the lighting and extinguishing of the strobo light source 98, the incident light is received during the transfer period of the signal charges, thus preventing the smear phenomenon.

Figure 21:
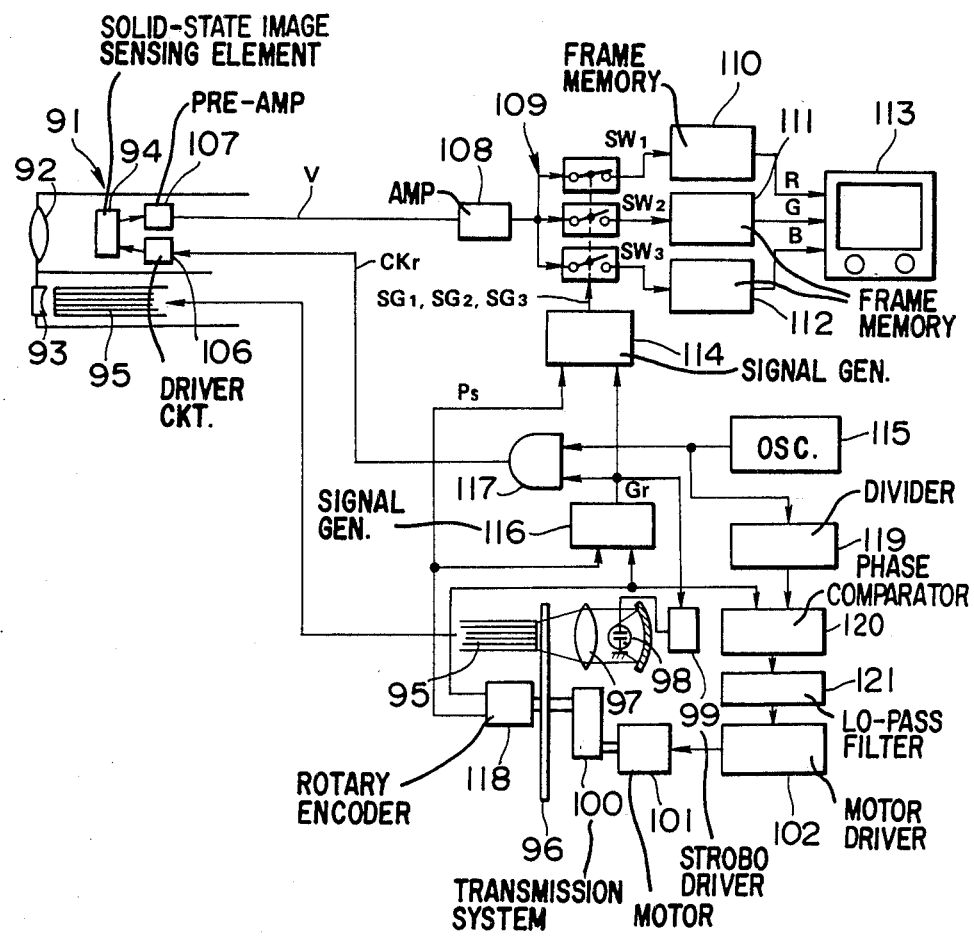
FIG. 21 is a block diagram to show a sixth Embodiment of this invention.

FIG. 21 shows a sixth Embodiment of this invention. The makeup of the rotary filter 96 is same as the one shown in FIG. 19 but instead of the start pulse detector 104 and readout pulse detector 105, a rotary encoder 118 is provided on the rotating shaft of the rotary filter 96 and the readout gate signal Gr is produced by the readout gate signal generator 116 using the detection signal detected by the rotary encoder 118 and the start pulse Ps, and the detection signal of the rotary encoder 118 and the signal from the oscillator 115 divided by the divider 119 are input to the phase comparator 120 to detect the phase difference. The detected signal is then fed back to the motor driver 102 via the low pass filter circuit 121 to control the rotating speed of the motor 101 to be constant. The other circuit makeup than the above remains completely same as that in FIG. 17.

In FIG. 19 one each of the R, G and B color filters 96R, 96G and 96B is arranged on the rotary filter 96 on the same circumference, but it is also possible that multiple color filter sets are arranged on the same circumference. But when multiple sets are arranged, it is necessary to make the circumferential length of each color filter longer than the range $Rt_1$ required to accumulate the video signals in the solid state image sensing element so that the extra portion can be made the video signal readout period $Rt_2$. Although in FIG. 19 the R, G and B color filters 96R, 96G and 96B are arranged like a band adjacent to each other on the same circumference, it is also possible to for the portion equivalent to the video signal readout period $Rt_2$ of a shielding plate, thus providing shielding region between the color filters. The shape of the color filter is not limited to the band-like shape.

It is clear that many more embodiments can be formed without conflicting with the spirit and scope of this invention and this invention is not limited to the particular embodiments except the limitations described in the claims.

We claim:
1. An endoscope, comprising:
an inserting member having an end component;
a light source means for projecting light through said inserting member and onto a subject;
a line transfer type solid-state image sensing means disposed in said end component for receiving the optical image of the subject illuminated by said light source means, and for converting said receiving image into electrical signals;
a light control means for controlling the light incident on said solid-state image sensing means and a signal charge accumulated in said solid-state image sensing means during the incident period when reflected light is incident on said solid-state image sensing means, such that said reflected light is controlled so that it is not incident on said image sensing means when said signal charge is being read out from said image sensing means, and wherein said light control means includes means for generating sequential lighting for each frame using light of the wavelength of each of the three primary colors, said generating means including a rotary filter disposed in the path of said projected light, said rotary filter having red, blue and green transmitting regions arranged between alternate shielding regions such that as said filter rotates, white light passing through said transmitting regions is sequentially changed to each one of said primary colors, each of said red, blue and green transmitting regions on said rotary filter having concave ends to minimize the rise and fall time of the quantity of light transmitted therethrough; and
a monitor for displaying, in color, the subject image on the basis of electrical signals read out from said solid-state image sensing means.
2. The endoscope of claim 1, wherein said shielding regions are made variable such that the size of said transmitting regions are adjustable.
3. The endoscope of claim 1, including,
a first detecting element for detecting a single rotation of said rotary filter,
a second detecting element for detecting the occurrence of each shielding period created by each of said shielding regions, and
means responsive to signals from said first and second detecting elements for providing a signal to said light control means to initiate the reading of said accumulated signal charge from said image sensing means.

* * * * *